United States Patent
Freeman et al.

[11] Patent Number: 5,856,257
[45] Date of Patent: Jan. 5, 1999

[54] OLEFIN PRODUCTION

[75] Inventors: Jeffrey W. Freeman, Bartlesville, Okla.; John L. Buster, Caney, Kans.; Ronald D. Knudsen, Bartlesville, Okla.

[73] Assignee: Phillips Petroleum Company, Bartlesville, Okla.

[21] Appl. No.: 857,787

[22] Filed: May 16, 1997

[51] Int. Cl.⁶ ............................................. B01J 31/00
[52] U.S. Cl. ................... 502/152; 502/117; 502/120; 502/123; 502/150; 502/151; 502/153; 502/154; 502/155; 502/157; 502/167
[58] Field of Search ................................. 502/117, 120, 502/123, 150, 151, 152, 153, 154, 155, 157, 167

[56] References Cited

U.S. PATENT DOCUMENTS

| | | | |
|---|---|---|---|
| 5,331,070 | 7/1994 | Pettijohn et al. | 526/105 |
| 5,331,104 | 7/1994 | Reagen et al. | 585/512 |
| 5,340,785 | 8/1994 | Reagen et al. | 502/109 |
| 5,360,879 | 11/1994 | Reagen et al. | 526/129 |
| 5,376,612 | 12/1994 | Reagen et al. | 502/104 |
| 5,382,738 | 1/1995 | Reagen et al. | 585/512 |
| 5,393,719 | 2/1995 | Pettijohn et al. | 526/105 |
| 5,399,539 | 3/1995 | Reagen et al. | 502/107 |
| 5,438,027 | 8/1995 | Reagen et al. | 502/117 |
| 5,451,645 | 9/1995 | Reagen et al. | 526/97 |
| 5,491,272 | 2/1996 | Tanaka et al. | 585/520 |
| 5,523,507 | 6/1996 | Reagen et al. | 585/513 |
| 5,557,026 | 9/1996 | Tanaka et al. | 585/522 |
| 5,563,312 | 10/1996 | Knudsen et al. | 585/510 |
| 5,689,028 | 11/1997 | Lashier et al. | 585/512 |

*Primary Examiner*—Elizabeth D. Wood
*Attorney, Agent, or Firm*—Lynda S. Jolly

[57] ABSTRACT

A process is provided to modify an olefin production catalyst system which comprises contacting an olefin production catalyst system with ethylene prior to use. A process also is provided to trimerize and/or oligomerize olefins with the novel, modified olefin catalyst production system. The modified olefin production catalyst system produces less solids, such as, for example, polymer.

12 Claims, No Drawings

OLEFIN PRODUCTION

BACKGROUND OF THE INVENTION

This invention relates to olefin production and olefin production catalyst system improvements.

Olefins, primarily alpha-olefins, have many uses. In addition to uses as specific chemicals, alpha-olefins, especially mono-1-olefins, are used in polymerization processes either as monomers or comonomers to prepare polyolefins, or polymers. These alpha-olefins usually are used in a liquid or gas state. Unfortunately, very few efficient processes to selectively produce a specifically desired alpha-olefin are known. Furthermore, during many known olefin production processes, undesirable solid by-products can be produced. These undesirable solid by-products can be produced either during catalyst system preparation as fine, particulate contaminants or during olefin production as oligomeric or polymeric particulates. These undesirable solid by-products such as polymers or small, particulate impurities can lower the heat transfer coefficient of the reactor and/or can plug valves and piping downstream of the reactor vessel. Such problems can result in a decrease of olefin production due to the need to shut down the reactor to clean valves, piping and even the fouled reactor.

SUMMARY OF THE INVENTION

Accordingly, it is an object of this invention to provide an improved olefin production process.

It is another object of this invention to provide an improved olefin production process that has decreased, or no, solids or polymer production.

It is a further object of this invention to provide an improved olefin production catalyst system that produces little or no undesirable solid particulates during catalyst system preparation.

It is yet another object of this invention to provide an improved olefin production catalyst system that produces little or no polymeric by-products during olefin production processes.

In accordance with this invention, a process is provided to produce an olefin production catalyst system that produces little, or no solid by-products during catalyst system preparation.

In accordance with still another embodiment of this invention, a process is provided to produce olefins wherein little, or no or solid by-products are produced.

DETAILED DESCRIPTION OF THE INVENTION

Catalyst Systems

Catalyst systems useful in accordance with this invention comprise a chromium source, a pyrrole-containing compound and a metal alkyl, all of which have been contacted and/or reacted in the presence of an unsaturated hydrocarbon. Optionally, these catalyst systems can be supported on an inorganic oxide support. These catalyst systems are especially useful for the dimerization and trimerization of olefins, such as, for example, ethylene to 1-hexene. Unless otherwise stated, the preferred catalyst system of this invention is a homogeneous catalyst system. Optionally, known catalyst system supports can be used to produce heterogeneous catalyst systems. It should be noted that the catalyst system is both air and water sensitive. All work with catalyst systems should be done under inert atmosphere conditions, such as nitrogen, using anhydrous, degassed solvents.

The chromium source can be one or more organic or inorganic compounds, wherein the chromium oxidation state is from 0 to 6. Generally, the chromium source will have a formula of $CrX_n$, wherein X can be the same or different and can be any organic or inorganic radical, and n is an integer from 1 to 6. Exemplary organic radicals can have from about 1 to about 20 carbon atoms per radical, and are selected from the group consisting of alkyl, alkoxy, ester, ketone, and/or amido radicals. The organic radicals can be straight-chained or branched, cyclic or acyclic, aromatic or aliphatic, can be made of mixed aliphatic, aromatic, and/or cycloaliphatic groups. Exemplary inorganic radicals include, but are not limited to halides, sulfates, and/or oxides.

Preferably, the chromium source is a chromium(II)- and/or chromium(III)-containing compound which can yield a catalyst system with improved trimerization or oligomerization activity. Most preferably, the chromium source is a chromium(III) compound because of ease of use, availability, and enhanced catalyst system activity. Exemplary chromium(III) compounds include, but are not limited to, chromium carboxylates, chromium naphthenates, chromium halides, chromium pyrrolides, and/or chromium dionates. Specific exemplary chromium(III) compounds include, but are not limited to, chromium(III) 2,2,6,6,-tetramethylheptanedionate [Cr(TMHD)], chromium(III) 2-ethylhexanoate [Cr(EH) or chromium(III) tris(2-ethylhexanoate),] chromium(III) naphthenate [Cr(Np)], chromium(III) chloride, chromic bromide, chromic fluoride, chromium(III) acetylacetonate, chromium(III) acetate, chromium(III) butyrate, chromium(III) neopentanoate, chromium(III) laurate, chromium(III) stearate, chromium(III) pyrrolides and/or chromium(III) oxalate.

Specific exemplary chromium(II) compounds include, but are not limited to, chromous bromide, chromous fluoride, chromous chloride, chromium(II) bis(2-ethylhexanoate), chromium(II) acetate, chromium(II) butyrate, chromium(II) neopentanoate, chromium(II) laurate, chromium(II) stearate, chromium(II) oxalate and/or chromium(II) pyrrolides.

The pyrrole-containing compound can be any pyrrole-containing compound, or pyrrolide, that will react with a chromium source to form a chromium pyrrolide complex. As used in this disclosure, the term "pyrrole-containing compound" refers to hydrogen pyrrolide, i.e., pyrrole $(C_5H_5N)$, derivatives of hydrogen pyrrolide, substituted pyrrolides, as well as metal pyrrolide complexes. A "pyrrolide" is defined as a compound comprising a 5-membered, nitrogen-containing heterocycle, such as for example, pyrrole, derivatives of pyrrole, and mixtures thereof. Broadly, the pyrrole-containing compound can be pyrrole and/or any heteroleptic or homoleptic metal complex or salt, containing a pyrrolide radical, or ligand. The pyrrole-containing compound can be either affirmatively added to the reaction, or generated in-situ.

Generally, the pyrrole-containing compound will have from about 4 to about 20 carbon atoms per molecule. Exemplary pyrrolides are selected from the group consisting of hydrogen pyrrolide (pyrrole), lithium pyrrolide, sodium pyrrolide, potassium pyrrolide, cesium pyrrolide, aluminum pyrrolide, and/or the salts of substituted pyrrolides, because of high reactivity and activity with the other reactants. Examples of substituted pyrrolides include, but are not limited to, pyrrole-2-carboxylic acid, 2-acetylpyrrole, pyrrole-2-carboxaldehyde, tetrahydroindole, 2,5-dimethylpyrrole, 2,4-dimethyl-3-ethylpyrrole, 3-acetyl-2,4-dimethylpyrrole, ethyl-2,4-dimethyl-5-(ethoxycarbonyl)-3-pyrrole-proprionate, ethyl-3,5-dimethyl-2-pyrrolecarboxylate, and mixtures thereof. When the pyrrole-containing compound contains chromium, the resultant chromium compound can be called a chromium pyrrolide.

The most preferred pyrrole-containing compounds used in a trimerization catalyst system are selected from the group consisting of hydrogen pyrrolide, i.e., pyrrole ($C_5H_5N$), 2,5-dimethylpyrrole and/or chromium pyrrolides because of enhanced trimerization activity. Optionally, for ease of use, a chromium pyrrolide can provide both the chromium source and the pyrrole-containing compound. As used in this disclosure, when a chromium pyrrolide is used to form a catalyst system, a chromium pyrrolide is considered to provide both the chromium source and the pyrrole-containing compound. While all pyrrole-containing compounds can produce catalyst systems with high activity and productivity, use of pyrrole and/or 2,5-dimethylpyrrole can produce a catalyst system with enhanced activity and selectivity to a desired product.

The metal alkyl can be any heteroleptic or homoleptic metal alkyl compound. One or more metal alkyls can be used. The alkyl ligand(s) on the metal can be aliphatic and/or aromatic. Preferably, the alkyl ligand(s) are any saturated or unsaturated aliphatic radical. The metal alkyl can have any number of carbon atoms. However, due to commercial availability and ease of use, the metal alkyl will usually comprise less than about 70 carbon atoms per metal alkyl molecule and preferably less than about 20 carbon atoms per molecule. Exemplary metal alkyls include, but are not limited to, alkylaluminum compounds, alkylboron compounds, alkylmagnesium compounds, alkylzinc compounds and/or alkyl lithium compounds. Exemplary metal alkyls include, but are not limited to, n-butyl lithium, s-butyllithium, t-butyllithium, diethylmagnesium, diethylzinc, triethylaluminum, trimethylaluminum, triisobutylalumium, and mixtures thereof.

Preferably, the metal alkyl is selected from the group consisting of non-hydrolyzed, i.e., not pre-contacted with water, alkylaluminum compounds, derivatives of alkylaluminum compounds, halogenated alkylaluminum compounds, and mixtures thereof for improved product selectivity, as well as improved catalyst system reactivity, activity, and/or productivity. The use of hydrolyzed metal alkyls can result is decreased olefin, i.e., liquids, production and increased polymer, i.e., solids, production.

Most preferably, the metal alkyl is a non-hydrolyzed alkylaluminum compound, expressed by the general formulae $AlR_3$, $AlR_2X$, $AlRX_2$, $AlR_2(OR)$, and/or $AlRX(OR)$, wherein R is an alkyl group and X is a halogen atom. Exemplary compounds include, but are not limited to, triethylaluminum, tripropylaluminum, tributylaluminum, diethylaluminum chloride, diethylaluminum bromide, diethylaluminum ethoxide, diethylaluminum phenoxide, ethylaluminum dichloride, ethylaluminum sesquichloride, and mixtures thereof for best catalyst system activity and product selectivity. The most preferred alkylaluminum compound is triethylaluminum, for best results in catalyst system activity and product selectivity.

Catalyst System Preparation

In accordance with the present invention, preparation of the catalyst system is critical. Usually, contacting and/or reacting of the chromium source, pyrrole-containing compound and a metal alkyl is done in the presence of an unsaturated hydrocarbon. The unsaturated hydrocarbon can be any aromatic or aliphatic hydrocarbon, in a gas, liquid or solid state. Preferably, to effect thorough contacting of the chromium source, pyrrole-containing compound, and metal alkyl, the unsaturated hydrocarbon is a liquid.

The unsaturated hydrocarbon can have any number of carbon atoms per molecule. Usually, the unsaturated hydrocarbon will comprise less than about 70 carbon atoms per molecule, and preferably, less than about 20 carbon atoms per molecule, due to commercial availability and ease of use. Exemplary unsaturated, aliphatic hydrocarbon compounds include, but are not limited to, ethylene, 1-hexene, 1,3-butadiene, and mixtures thereof. The most preferred unsaturated aliphatic hydrocarbon compounds are ethylene and 1-hexene, because of elimination of catalyst system preparation steps and 1-hexene can be a reaction product. Exemplary unsaturated aromatic hydrocarbons include, but are not limited to, toluene, benzene, xylene, mesitylene, ethylbenzene, hexamethylbenzene, and mixtures thereof. Unsaturated, aromatic hydrocarbons are preferred in order to improve catalyst system stability, as well as produce a highly active and selective catalyst system. The most preferred unsaturated aromatic hydrocarbons are selected from the group consisting of toluene, ethylbenzene and mixtures thereof for best catalyst system activity, selectivity and productivity, as well as best compatibility with an olefin production process.

The order of addition of the catalyst system components in accordance with this invention is critical because certain addition orders can improve catalyst system reactivity, selectivity and productivity. The chromium compound and pyrrole-containing compound are contacted first to form a chromium pyrrolide reaction mixture and then the alkylaluminum compound is added to the chromium pyrrolide reaction mixture.

During contacting of the catalyst components, heat can be generated by a variety of exothermic reactions. Usually, stirring is the most efficient method to disperse excess heat of reaction. Unfortunately, during preparation of the catalyst system it has been found that stirring can be detrimental to the catalyst system either by creating fine, solid particulates, i.e., a precipitate, or stirring can cause these particulates to become suspended in the catalyst system preparation solution. Even though it is possible to remove the fine particulate precipitate by filtration, the particles are so fine that the particles can clog removal filters. Thus, in accordance with this invention, in order to minimize the quantity of particulates generated by catalyst system preparation or to make removal of the particulates possible, little or no stirring of the catalyst system preparation solution should occur. In other words, in order to minimize or eliminate the quantity of solid precipitate generated by stirring, the catalyst system is prepared with no or very low speed stirring.

In addition to the production of fine particulates during catalyst system preparation, it also has been found that stirring of the catalyst system during preparation can cause the formation of polymer particles during trimerization or oligomerization using the stirred catalyst system. Formation of polymer is detrimental to an efficient trimerization or oligomerization process because of loss of heat transfer and the necessity for removal of polymer from the desired olefinic product.

Usually, if mechanical stirring is used, the speed of stirring is less than 100 rotations per minute (rpm), preferably, less than 50 rpm. Most preferably, the catalyst system is prepared in the absence of mechanical stirring in order to most effectively reduce the amount of fine particulates generated during catalyst system preparation, as well as decrease the amount of polymer formed during the oligomerization reaction. In this manner, catalyst system preparation can be simplified both by not stirring and no need to filter to remove fine particulates. Preferably, however, the resultant homogeneous catalyst system can be filtered, or decanted, to remove any larger particulates that form during catalyst system preparation.

It should be recognized, however, that the reaction mixture comprising a chromium source, pyrrole-containing compound, metal alkyl and unsaturated hydrocarbon can contain additional components which do not adversely affect and can enhance the resultant catalyst system, such as, for example, halides. As alluded to earlier, catalyst system supports also can be added during catalyst system preparation to produce a supported, heterogeneous catalyst system.

Even though the catalyst system preferably can be produced in the presence of an unsaturated hydrocarbon, additional, beneficial catalyst system improvements can be achieved by precontacting the catalyst system with some ethylene prior to the olefin production reaction. Precontacting the catalyst system and ethylene can occur in accordance with any method known in the art and at anytime prior to contacting the catalyst system with one of the reactants, such as, for example, ethylene, and prior to the introduction of heat to the catalyst system. Therefor, the ethylene and catalyst system can be precontacted either outside the reactor or in-situ in the reactor.

After precontacting ethylene with the catalyst system, some solids will be formed. The catalyst system solution preferably is filtered before further contacting reactants, such as additional ethylene, to produce olefins. While not wishing to be bound by theory, it is believed that filtering can remove undesirable solids that can foul the reactor. It also is believed that removal of undesirable solids can decrease additional solids formation. In order for ease of filtering, it is preferred that ethylene and catalyst system are precontacted before introduction of the catalyst system into the olefin production reactor.

Reactants

Trimerization, as used in this disclosure, is defined as the combination of any two, three, or more olefins, wherein the number of olefin, i.e., carbon-carbon double bonds is reduced by two. Reactants applicable for use in the trimerization process of this invention are olefinic compounds which can a) self-react, i.e., trimerize, to give useful products such as, for example, the self reaction of ethylene can give 1-hexene and the self-reaction of 1,3-butadiene can give 1,5-cyclooctadiene; and/or b) olefinic compounds which can react with other olefinic compounds, i.e., co-trimerize, to give useful products such as, for example, co-trimerization of ethylene plus hexene can give 1-decene and/or 1-tetradecene, co-trimerization of ethylene and 1-butene can give 1-octene, co-trimerization of 1-decene and ethylene can give 1-tetradecene and/or 1-docosene. For example, the number of olefin bonds in the combination of three ethylene units is reduced by two, to one olefin bond, in 1-hexene. In another example, the number of olefin bonds in the combination of two 1,3-butadiene units, is reduced by two, to two olefin bonds in 1,5-cyclooctadiene. As used herein, the term "trimerization" is intended to include dimerization of diolefins, as well as "co-trimerization", both as defined above.

Suitable trimerizable olefin compounds are those compounds having from about 2 to about 30 carbon atoms per molecule and having at least one olefinic double bond. Exemplary mono-1-olefin compounds include, but are not limited to acyclic and cyclic olefins such as, for example, ethylene, propylene, 1-butene, 2-butene, isobutylene, 1-pentene, 2-pentene, 1-hexene, 2-hexene, 3-hexene, 1-heptene, 2-heptene, 3-heptene, the four normal octenes, the four normal nonenes, and mixtures of any two or more thereof. Exemplary diolefin compounds include, but are not limited to, 1,3-butadiene, 1,4-pentadiene, and 1,5-hexadiene. If branched and/or cyclic olefins are used as reactants, while not wishing to be bound by theory, it is believed that steric hindrance could hinder the trimerization process. Therefore, the branched and/or cyclic portion(s) of the olefin preferably should be distant from the carbon-carbon double bond.

Catalyst systems produced in accordance with this invention preferably are employed as trimerization catalyst systems.

Reaction Conditions

The reaction products, i.e., olefin trimers as defined in this specification, can be prepared from the catalyst systems of this invention by solution reaction, slurry reaction, and/or gas phase reaction techniques using conventional equipment and contacting processes. Contacting of the monomer or monomers with a catalyst system can be effected by any manner known in the art. One convenient method is to suspend the catalyst system in an organic medium and to agitate the mixture to maintain the catalyst system in solution throughout the trimerization process. Other known contacting methods can also be employed.

Reaction temperatures and pressures can be any temperature and pressure which can trimerize the olefin reactants. Generally, reaction temperatures are within a range of about 0° to about 250° C. Preferably, reaction temperatures within a range of about 60° to about 200° C. and most preferably, within a range of 80° to 150° C. are employed. Generally, reaction pressures are within a range of about atmospheric to about 2500 psig. Preferably, reaction pressures within a range of about atmospheric to about 1000 psig and most preferably, within a range of 300 to 800 psig are employed.

Too low of a reaction temperature can produce too much undesirable insoluble product, such as, for example, polymer, and too high of a temperature can cause decomposition of the catalyst system and reaction products. Too low of a reaction pressure can result in low catalyst system activity.

Optionally, hydrogen can be added to the reactor to accelerate the reaction and/or increase catalyst system activity.

Catalyst systems of this invention are particularly suitable for use in trimerization processes. The slurry process is generally carried out in an inert diluent (medium), such as a paraffin, cycloparaffin, or aromatic hydrocarbon. Exemplary reactor diluents include, but are not limited to, isobutane, cyclohexane and 1-hexene. Isobutane can be used to improve process compatibility with other known olefin production processes. However, a homogenous trimerization catalyst system is more soluble in cyclohexane or methylcyclohexane. Therefore, preferred diluents for homogeneous catalyzed trimerization processes are cyclohexane, methylcyclohexane and mixtures thereof If 1-hexene, a possible trimerization product, is used as the reactor diluent, then separation of 1-hexene (reaction product) from the diluent (1-hexene) is unnecessary. When the reactant is predominately ethylene, a temperature in the range of about 0° to about 300° C. generally can be used. Preferably, when the reactant is predominately ethylene, a temperature in the range of about 60° to about 120° C. is employed.

Products

The olefinic products of this invention have established utility in a wide variety of applications, such as, for example, as monomers for use in the preparation of homopolymers, copolymers, and/or terpolymers.

The further understanding of the present invention and its advantages will be provided by reference to the following examples.

EXAMPLES

Example A - Catalyst Preparation

The catalyst system is both air and water sensitive. All work should be done under inert atmosphere conditions (nitrogen) using anhydrous, degassed solvents. Seven catalyst systems were prepared as described below.

Run 1 201.7 grams of chromium tris(2-ethylhexanoate) ($Cr(EH)_3$) was dissolved in 1000 ml of toluene. This solution was charged to a 5 gallon reactor containing 13.7 lbs of toluene. Then, 125 ml of 2,5-dimethylpyrrole (2,5-DMP) was added to the chromium solution. The reactor was closed, the stirrer turned on, and the system was purged with nitrogen for 5 minutes (to remove any residual air). Next, 516 g of triethyl aluminum (TEA) and 396 g of diethylaluminum chloride (DEAC) were combined in a mix tank. The resulting aluminum alkyl mixture then was pressured into the 5 gallon reactor. Cooling water to the reactor was turned on and the contents of the reactor were stirred for one hour. While not wishing to be bound by theory, it is believed that the catalyst system can form within about five to about ten minutes of contacting all components.

After one hour, stirring was stopped and the solution was allowed to gravimetrically settle for 3 hours before filtration. The catalyst system solution was filtered through a celite and glass wool filter into a 5 gallon storage tank. A sample of the resultant, homogeneous catalyst system was visually inspected in a glove box and then tested under trimerization conditions. The observations are given in Table 1.

Run 2 The same procedure provided in Run 1 was followed except that a nitrogen purge was used to mix the reactor contents instead of a mechanical stirrer.

Run 3 The same procedure provided in Run 1 was followed except that reactor contents were not stirred during the reaction.

Run 4 630.9 grams of $Cr(EH)_3$ was dissolved in 1000 ml of ethylbenzene. This solution was charged to a 5 gallon reactor containing 17.9 lbs of ethylbenzene. Then, 233 ml of 2,5-DMP was added to the chromium solution. The reactor was closed, the stirrer turned on, and the system was purged with nitrogen for 5 minutes (to remove any residual air). Next, 953 g of TEA and 775 g of DEAC were combined in a mix tank. The resulting aluminum alkyl mixture then was pressured into the 5 gallon reactor. Cooling water to the reactor was turned on and the contents of the reactor were stirred for one hour. While not wishing to be bound by theory, it is believed that the catalyst system can form within about five to about ten minutes of contacting all components.

After one hour, stirring was stopped and the solution was allowed to gravimetrically settle for overnight before filtration. The catalyst system solution was filtered through a celite and glass wool filter into a 5 gallon storage tank. A sample of the resultant, homogeneous catalyst system was visually inspected in a glove box and then tested under trimerization conditions.

Run 5 The same procedure provided in Run 4 was followed except that the reactor contents were not stirred during the reaction.

Run 6 630.9 grams of $Cr(EH)_3$ was dissolved in 1000 ml of toluene. This solution was charged to a 5 gallon reactor containing 15.1 lbs of toluene. Then, 388 ml of 2,5-DMP was added to the chromium solution. The reactor was closed, the stirrer turned on, and the system was purged with nitrogen for 5 minutes (to remove any residual air). Next, 1600 g of TEA and 1229 g of DEAC were combined in a mix tank. The resulting aluminum alkyl mixture then was pressured into the 5 gallon reactor. The cooling water to the reactor was turned on and the contents of the reactor were not stirred. The cooling water was turned off when the reactor temperature reached 25° C. While not wishing to be bound by theory, it is believed that the catalyst system can form within about five to about ten minutes of contacting all components.

After one hour, stirring was stopped and the solution was allowed to gravimetrically settle for 3 hours before filtration. The catalyst system solution was filtered through a celite and glass wool filter into a 5 gallon storage tank. A sample of the resultant, homogeneous catalyst system was visually inspected in a glove box and then tested under trimerization conditions.

Run 7 The same procedure given in Run 6 was used except ethylbenzene was used in place of toluene.

TABLE 1

OBSERVATIONS

| Run | Stirring | Change in Temperature, C.° | Catalyst Preparation Solution Clarity |
|---|---|---|---|
| 1 | mechanical | +7 | black suspension; did not settle |
| 2 | nitrogen purge | +7 | black suspension; did not settle |
| 3 | none | +12 | clear orange |
| 4 | mechanical | +10 | black suspension; did not settle |
| 5 | none | not available | clear orange |
| 6 | none | +21 | clear orange |
| 7 | none | +19 | clear orange |

The data in Table 1 show that the absence of stirring results in a homogeneous catalyst system that does not have any solids, nor any suspended particulates. When the catalyst system is stirred during preparation, solids are produced and a black, particulate suspension is formed.

Example B - Trimerization Reactions

The trimerization of ethylene to 1-hexene was carried out in a 1-gallon continuous feed autoclave reactor. Cyclohexane was the process solvent and the reactor temperature was maintained at 115° C. for all runs. Catalyst was fed at a rate of 30 ml/hour. Each run lasted six (6) hours. At the end of each run, the reactor was opened and any polyethylene polymer that formed was collected, dried and weighed. Reactor conditions for each run are provided in Table 2. Analyses of products are provided in Table 3.

TABLE 2

REACTOR CONDITIONS

| Run | Residence time of reaction mixture, hours | Ethylene feed rate, grams/hr | Solvent feed rate, gallons/hr | Hydrogen feed rate, liters/hr | Reactor pressure, psia | Catalyst concentration, mg Cr/ml catalyst system solution fed to reactor |
|---|---|---|---|---|---|---|
| 1 | 0.61 | 1959 | 0.47 | 19.6 | 1450 | 0.5 |
| 2 | 0.61 | 1959 | 0.47 | 19.6 | 1450 | 0.5 |
| 3 | 0.61 | 1959 | 0.47 | 19.6 | 1450 | 0.5 |
| 4 | 0.42 | 1426 | 1.17 | 5.2 | 800 | 0.8 |

TABLE 2-continued

REACTOR CONDITIONS

| Run | Residence time of reaction mixture, hours | Ethylene feed rate, grams/hr | Solvent feed rate, gallons/hr | Hydrogen feed rate, liters/hr | Reactor pressure, psia | Catalyst concentration, mg Cr/ml catalyst system solution fed to reactor |
|---|---|---|---|---|---|---|
| 5 | 0.42 | 1426 | 1.17 | 5.2 | 800 | 0.8 |
| 6 | 0.42 | 1426 | 1.17 | 5.2 | 800 | 0.8 |
| 7 | 0.42 | 1426 | 1.17 | 5.2 | 800 | 0.8 |

TABLE 3

ANALYTICAL RESULTS OF PRODUCTS (in weight percent)

| Run | Stirring Method | Weight % Butene | Weight %1-Hexene | Weight % Internal Hexenes | Weight % Octenes | Weight % Decenes | Weight % Heavier | % Ethylene Conversion | Productivity, g olefins/g Cr | Total Polymer, g |
|---|---|---|---|---|---|---|---|---|---|---|
| 1 | mechanical | 0.48 | 93.69 | 0.75 | 0.45 | 4.48 | 0.16 | 58.1 | 71400 | 1.72 |
| 2 | nitrogen purge | 0.17 | 93.08 | 0.75 | 0.32 | 5.38 | 0.29 | 77.6 | 94700 | 1.42 |
| 3 | none | 0.44 | 87.76 | 1.02 | 0.38 | 9.55 | 0.85 | 80.7 | 92800 | 0.92 |
| 4 | mechanical | 0.11 | 81.88 | 0.62 | 0.03 | 16.09 | 1.26 | 84.9 | 41200 | 1.77 |
| 5 | none | 0.11 | 84.54 | 0.71 | 0.25 | 13.30 | 1.09 | 86.6 | 43400 | 2.36 |
| 6 | none | 0.20 | 88.36 | 1.07 | 0.22 | 9.54 | 0.61 | 82.5 | 43200 | 0.62 |
| 7 | none | 0.28 | 89.01 | 1.18 | 0.28 | 8.56 | 0.70 | 83.5 | 44000 | 0.69 |

The data in Table 3 show that mechanical stirring results, not only in production of solid particulates, as shown in Table 1, but also higher production of undesirable polymer products. Nitrogen purging, which is a less aggressive mixing technique than mechanical stirring, also results in polymer production and formation, but less than under conditions of mechanical stirring. When no external processes are used for stirring, polymer production significantly decreases. Run 5 is an anomaly and it is believed that impurities were present in the cyclohexane trimerization process solvent, thus accounting for the high production of polymer during trimerization.

While this invention has been described in detail for the purpose of illustration, it is not to be construed as limited thereby but is intended to cover all changes and modifications within the spirit and scope thereof.

That which is claimed is:

1. A process to prepare a homogenous olefin production catalyst system comprising first contacting a chromium source and a pyrrole-containing compound and then adding a metal alkyl while stirring at a rate of less than 100 rotations per minute (rpm).

2. A process according to claim 1 wherein said chromium source is selected from the group consisting of chromium (II)-containing compound, a chromium(III)-containing compound, and mixtures thereof.

3. A process according to claim 2 wherein said chromium source is a chromium(III)-containing compound selected from the group selected of chromium carboxylates, chromium naphthenates, chromium halides, chromium pyrrolides, chromium dionates and mixtures of two or more thereof.

4. A process according to claim 3 wherein chromium source is selected from the group consisting of chromium (III) 2,2,6,6,-tetramethylheptanedionate [Cr(TMHD)], chromium(III) 2-ethylhexanoate [Cr(EH) or chromium(III) tris(2-ethylhexanoate),] chromium(III) naphthenate [Cr(Np)], chromium(III) chloride, chromic bromide, chromic fluoride, chromium(III) acetylacetonate, chromium(III) acetate, chromium(III) butyrate, chromium(III) neopentanoate, chromium(III) laurate, and mixtures of two or more thereof, chromium(III) stearate, chromium (III) pyrrolides and/or chromium(III) oxalate.

5. A process according to claim 1 wherein said metal alkyl is a non-hydrolyzed metal alkyl and is selected from the group consisting of alkyl aluminum compounds, alkyl magnesium compounds, alkyl zinc compounds, alkyl lithium compounds, and mixtures of two or more thereof.

6. A process according to claim 5 wherein said non-hydrolyzed metal alkyl is an alkyl aluminum compound.

7. A process according to claim 6 wherein said alkyl aluminum compound is triethyl aluminum.

8. A process according to claim 1 wherein said pyrrole-containing compound is selected from the group consisting of pyrrole, derivatives of pyrrole, alkali metal pyrrolides, salts of alkali metal pyrrolides, and mixtures thereof.

9. A process according to claim 8 wherein said pyrrole-containing compound is selected from the group consisting of hydrogen pyrrolide, 2,5-dimethylpyrrole, and mixtures thereof.

10. A process according to claim 1 wherein said catalyst system further comprises a halide source.

11. A process according to claim 1 wherein said contacting occurs in the presence of an aromatic compound.

12. A process according to claim 11 wherein said aromatic hydrocarbon has less than about 70 carbon atoms per molecule.

* * * * *